United States Patent [19]

Moring et al.

[11] Patent Number: 5,239,360
[45] Date of Patent: Aug. 24, 1993

[54] LENS FOR CAPILLARY ELECTROPHORESIS AND CHROMATOGRAPHY

[75] Inventors: Stephen E. Moring, Sunnyvale; Dennis E. Mead, Campbell, both of Calif.

[73] Assignee: Applied Biosystems, Inc., Foster City, Calif.

[21] Appl. No.: 561,366

[22] Filed: Jul. 31, 1990

Related U.S. Application Data

[63] Continuation of Ser. No. 260,888, Oct. 21, 1988, abandoned.

[51] Int. Cl.$^5$ .................. G01N 21/01; G01N 21/64; G02B 9/02; G02B 13/14
[52] U.S. Cl. ........................... 356/344; 356/410; 359/355; 359/664; 250/461.1
[58] Field of Search ............... 356/344, 123, 127, 150, 356/239, 240, 39, 410; 350/416, 1.1, 1.2, 1.4; 250/458.1, 461.1, 461.2; 359/664, 350, 355

[56] References Cited

U.S. PATENT DOCUMENTS

| | | | |
|---|---|---|---|
| 3,663,395 | 5/1972 | Strickler | 356/344 |
| 3,864,571 | 2/1975 | Stillman et al. | 356/39 |
| 3,873,204 | 3/1975 | Friedman et al. | 356/39 |
| 3,916,205 | 10/1975 | Kleinerman | 356/39 |
| 4,062,996 | 12/1977 | Keafer, Jr. et al. | 350/1.6 |
| 4,156,570 | 5/1979 | Wardlaw | 356/39 |
| 4,242,194 | 12/1980 | Steiner et al. | 356/39 |
| 4,648,715 | 3/1987 | Ford, Jr. et al. | 356/344 |
| 4,660,971 | 4/1987 | Sage et al. | 356/39 |
| 4,675,300 | 6/1987 | Zare et al. | 356/344 |
| 4,714,345 | 12/1987 | Schrader | 356/246 |
| 4,747,687 | 5/1988 | Hoppe et al. | 356/410 X |
| 5,037,199 | 8/1991 | Hlousek | 356/410 X |

FOREIGN PATENT DOCUMENTS 0128327 7/1985 Japan .................. 356/344

Primary Examiner—Bruce Y. Arnold
Assistant Examiner—David R. Parsons
Attorney, Agent, or Firm—Joseph H. Smith; John A. Frazzini

[57] ABSTRACT

An apparatus for enhancing signal to noise ratio in the detection of electromagnetic radiation traversing a capillary tube includes a ball lens and a holding element for holding the ball lens and the capillary tube, the holding element having an aperture so that the aperature and the lens together define an optic axis. The holding element is configured to hold the capillary tube such that the center of the capillary tube traverses the optic axis. The lens has a focal length and is held at such a position relative to that focal length by the holding element such that electromagnetic radiation incident on the aperature is focussed to pass radially through the capillary tube. Thus, the effective path length is 100% of the inside diameter of the capillary tube.

9 Claims, 3 Drawing Sheets

LENS FOR CAPILLARY ELECTROPHORESIS AND CHROMATOGRAPHY

This application is a continuation, of application Ser. No. 07/260,888, filed Oct. 21, 1988, now abandoned.

BACKGROUND OF THE INVENTION

This invention pertains to an optical improvement for detecting absorbance and fluorescence in capillaries, and which is particularly useful for capillary electrophoresis and capillary liquid chromatography.

Generally, the sensitivity of ultraviolet detection which can be achieved by using transverse illumination of capillary tubes is limited because only a small fraction of the incident radiation falling on the tube actually passes through the center of the tube where the sample is located. This problem is illustrated more clearly in FIG. 1, which shows a cross-section of a fused silica capillary tube 101 having a center bore 102. (The typical outside plastic coating on the capillary is generally removed in a small region to allow the incident radiation to traverse the tube. Hence no outside coating is shown in the illustrated cross-section.) Several rays are shown, 103, 105, 107, and 109, which traverse the region of the capillary tube 101. In this example it will be assumed that the capillary tube 101 has an outside diameter of 375 μm, and an inside diameter of 50 μm, and that the incident beam has a diameter D of of 500 μm. As illustrated, only about 20 to 30% of the incident beam actually passes through the center of the tube and is detected by photodiode 111. Such a geometry provides an average path length of only about 0.6 times the inside diameter of the capillary tube, i.e. about 30.0 μm. Further, the detector cell volume, i.e. the volume inside of the capillary tube that is illuminated by the beam, is quite large. Both of these factors contribute deleteriously to the signal to noise ratio of the detection system.

What is needed is a detection scheme that maximizes path length and minimizes detector cell volume.

SUMMARY OF THE INVENTION

In accordance with preferred embodiments of the invention, an apparatus is provided for enhancing signal to noise ratio in the detection of electromagnetic radiation traversing a capillary tube by maximizing path length and minimizing detector cell volume. The apparatus includes a lens having the shape of a spherical ball and a holding element for holding this lens and the capillary tube, the holding element having an aperture so that the aperture and the lens together define an optic axis. The holding element is configured to hold the capillary tube such that the center of the capillary tube traverses the optic axis. The lens has a focal length and is held at such a position relative to that focal length by the holding element such that electromagnetic radiation incident on the aperture is focussed to pass radially through the capillary tube. Thus, the effective path length is 100% of the inside diameter of the capillary tube.

In a preferred embodiment, the apparatus is made up of two mating parts, a first part having the entrance aperture and configured for holding the lens, and a second part which when placed into juxtaposition with the first part holds the capillary tube so that the center of the capillary tube traverses the optic axis. The second part has an exit aperture for permitting detection of electromagnetic radiation that has traversed the capillary tube from the lens.

DETAILED DESCRIPTION OF THE PREFERRED EMBODIMENTS

Figure 1:
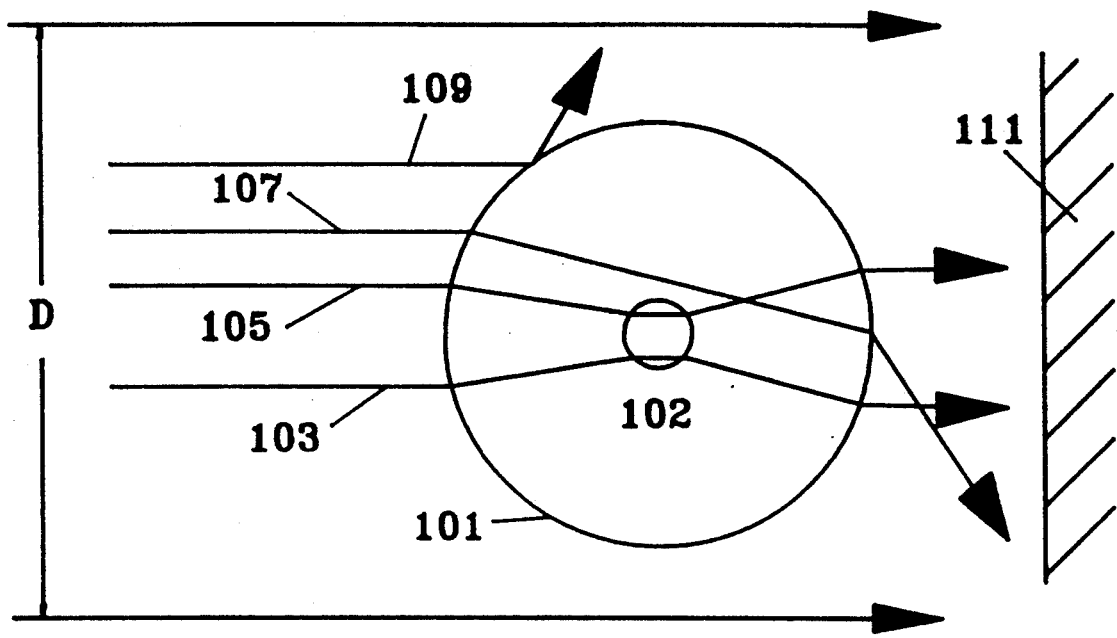
FIG. 1 shows the prior art configuration used for detection of radiation traversing a capillary tube.
Figure 2:
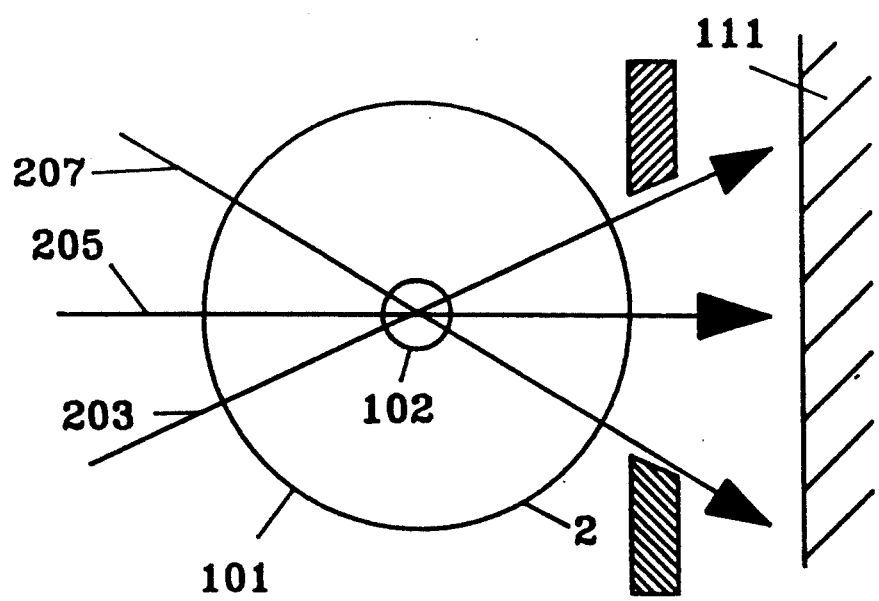
FIG. 2 shows the desired focussing of radiation on a capillary tube according to the invention.

In accordance with preferred embodiments of the invention, shown in FIG. 2 is a close up view of the cross-section of the capillary tube 101 with center bore 102 showing the incident radiation, illustrated by rays 203, 205, and 207, being focussed such that the rays pass radially through the center of the capillary. With this approach, the effective path length becomes essentially 100% of the inside diameter of the capillary tube. Also, the effective cell volume is dramatically reduced, typically by about 80% from that illustrated in FIG. 1.

Figure 3A:
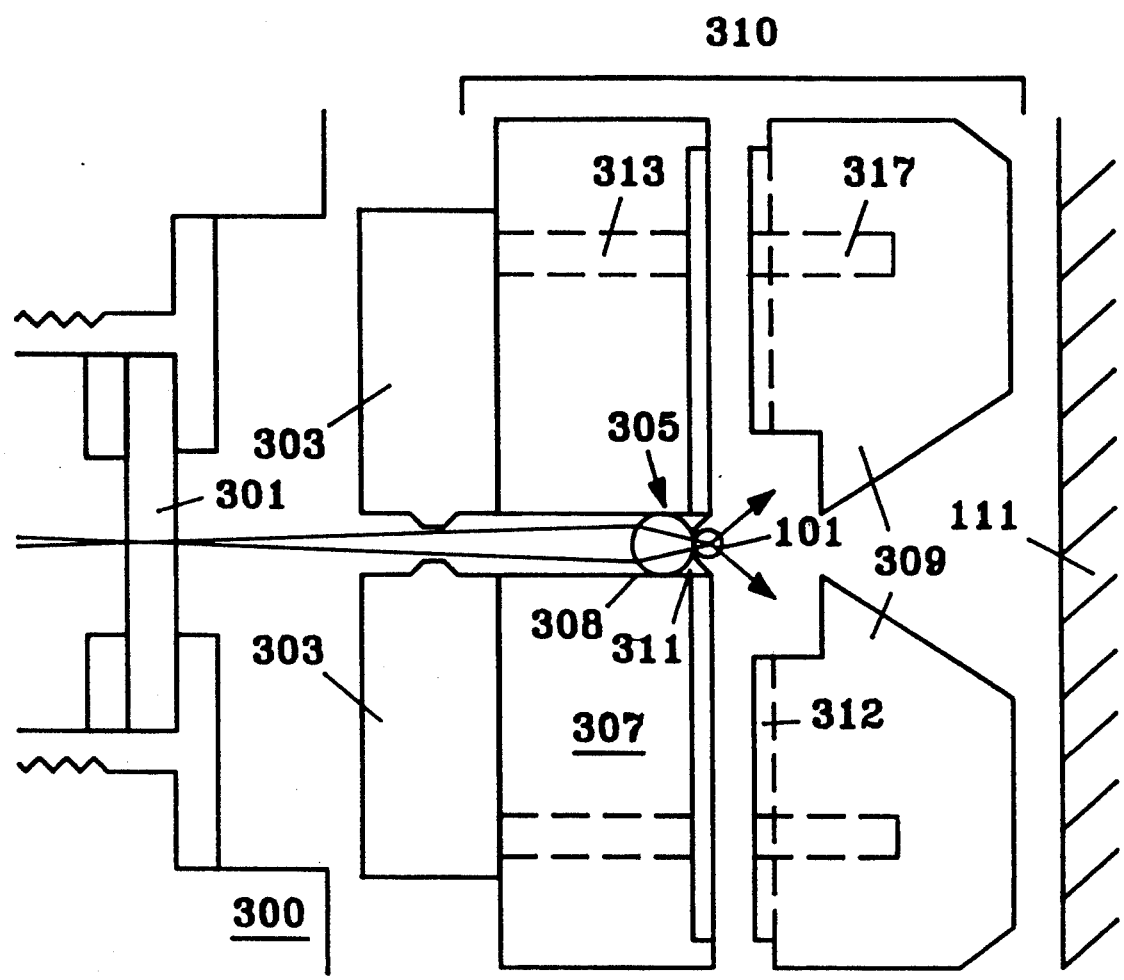
FIG. 3A shows a side view of an apparatus according to the invention for performing the focussing shown in FIG. 2.
Figures 3B, 3C:
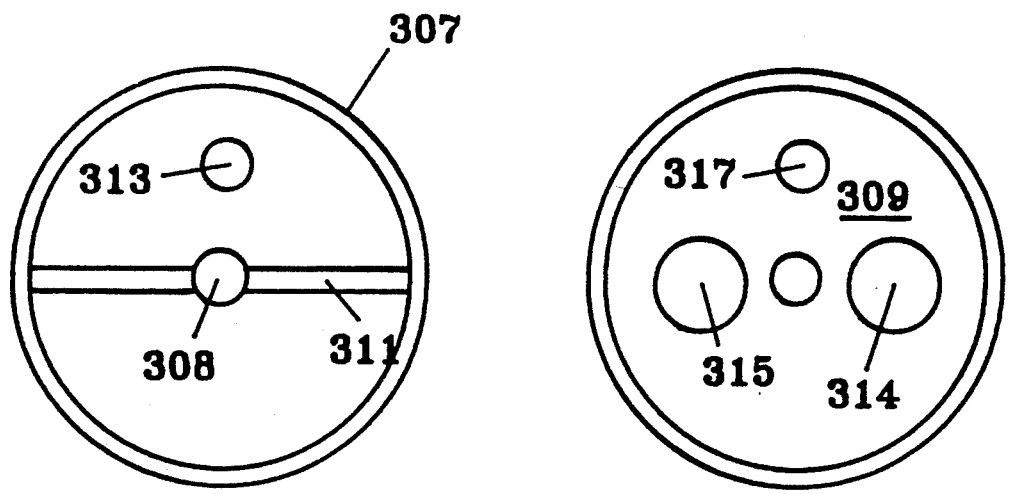
FIG. 3B shows an end view of a first mating part of the invention.
FIG. 3C shows an end view of a second mating part of the invention.

This radial geometry through the center of the capillary tube can be effected by the apparatus illustrated in FIGS. 3A, 3B and 3C. A source of incident radiation, typically from a deuterium or other source is focussed onto a grating and then reflected into a convergent beam, that is provided through a detector sample window 301 of a standard UV detector 300, for example an ABI model SPECTROFLOW ™ 700 Series UV Detector. The diameter of the incident beam is limited by an aperture 303, after which the incident beam enters a hole 308 that is bored into a lens holder section 307 of a UV cell 310. At the end of hole 308 is a lens 305, having the shape of a spherical ball and referred to herein as a "ball lens". Typically a sapphire ball, which is of such a diameter and such a location so as to focus the incident radiation radially through the center of the capillary 101. A second portion of the UV cell 310 is made up of a conical aperture 309 and a mating portion 312 which is configured to closely fit into lens holder section 307. Together these portions of the UV cell 310 are configured to fit into the standard UV detector 300.

The capillary tube 101 is positioned so that it is located on the optic axis of the system by a trapezoidal groove 311 cut across the axis of the cell 310. Two neoprene rubber pads 314 and 315 are used to tightly hold the capillary tube in the groove 311. The two mating parts of the UV cell 310 are held in place by a screw (not shown) which extends through hole 313 and into threaded hole 317. In the preferred mode, with capillary tube 101 having a 375 μm OD and a 50 μm ID, the preferred diameter of lens 305 is 2.0 mm. Sapphire is the preferred material since it is transparent to ultraviolet light (i.e. in the 190 to 400 nanometer wavelength region) and has a very high refractive index in that region (1.91 at 200 nm.) The aperture 303 upstream from the lens 305 in the preferred mode is typically 0.5 to 0.6 mm and is placed about 7 mm in front of the lens 305. The purpose of aperture 303 is to reduce gross aberrations. Also, using the dimensions above, the preferred position of the lens 305 is just touching the capillary tube outer diameter in order to achieve the radial focussing of the incident beam.

Generally, the lens is positioned by cutting the hole 308 somewhat smaller than the OD of the lens, for example to a diameter of 1.95 mm for a 2.0 mm lens, and then pressing the spherical lens 305 into the hole. This can be easily accomodated by using a relatively soft material such as plastic for the lens holder section 307, for example Acetal. For ease of manufacture, the conical aperture portion 309 is also typically constructed of plastic. The angle of the conical aperture portion is chosen to correspond to the maximum angle of radiation provided by lens 305, which with the above preferred dimensions corresponds to about 30 degrees from the optical axis. In that way the cone of light provided by the lens can be accomodated, but any light scattered outside that cone is filtered out. Thus light passing through the cell consists of only the light which has passed through the open central portion of the capilary. This cone of light then strikes the photodiode 111 imediately upon exiting the cell.

UTILITY OF THE INVENTION

The sensitivity of the above detection scheme as compared with the standard approach using a transversely illuminated capillary has been tested in two ways: First, by using static or stepwise absorbance measurement of a peptide and a protein solution, and second, by electrophoretically running the protein sample at 200 nm in the form of an input pulse.

Figure 4:
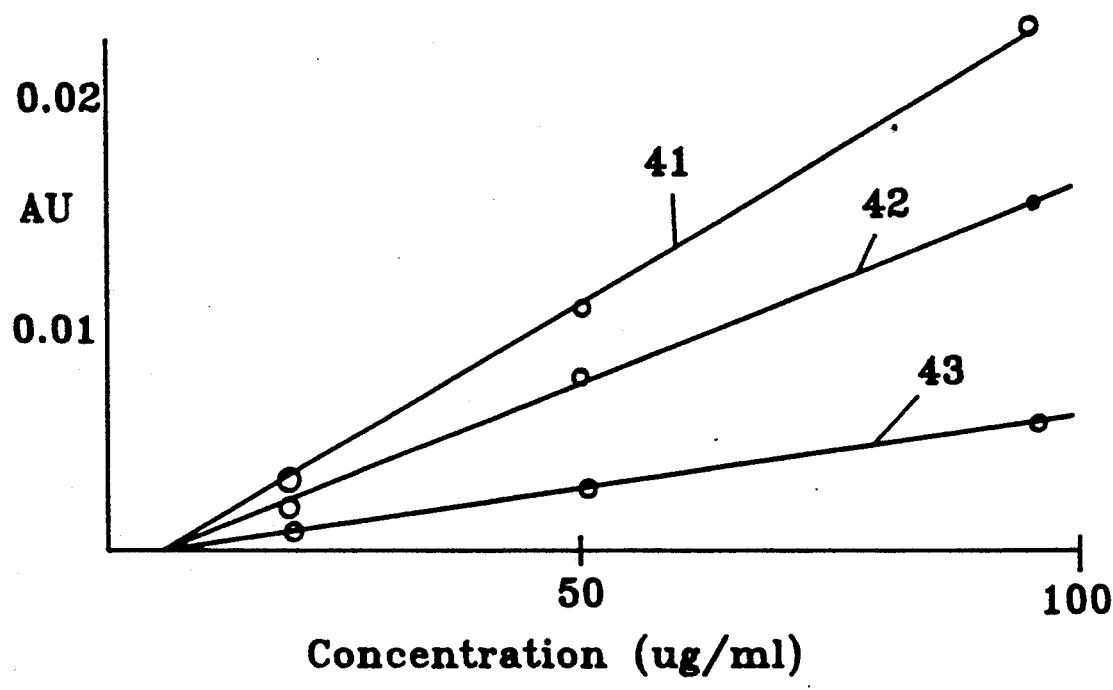
FIG. 4 shows the results of sensitivity experiments comparing the method of the invention and the prior art methods.
Figures 5A, 5B:
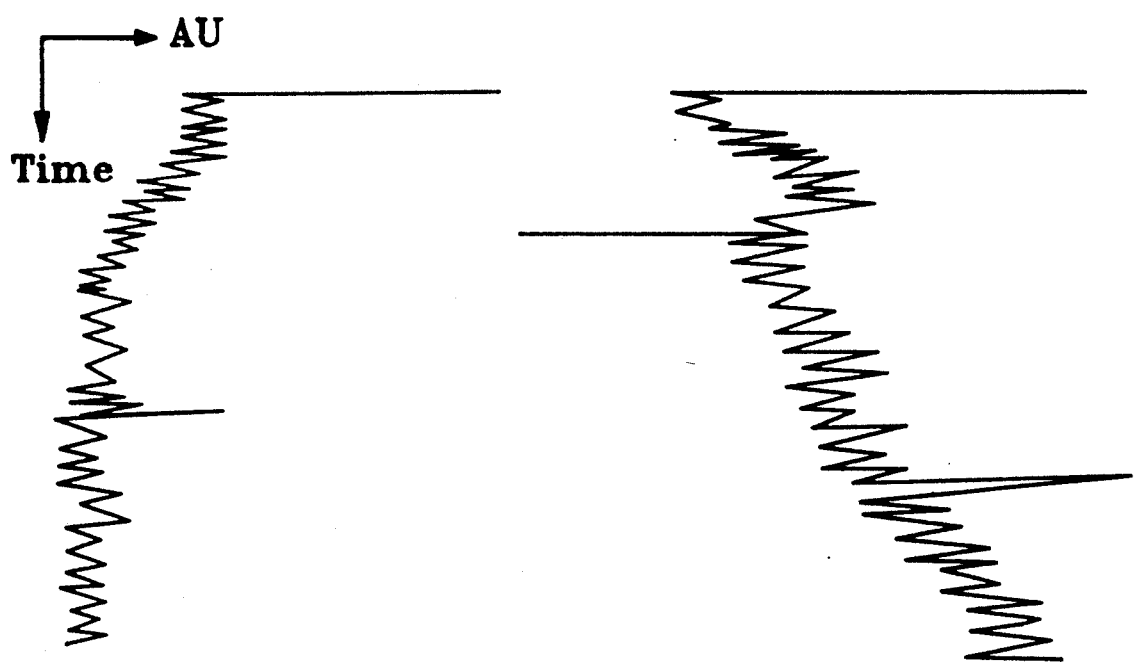
FIGS. 5A and 5B show shows the results on signal to noise ratio using the method of the invention compared to prior art methods.

In the former method, various concentrations of the peptide dynorphin were asperated into a 65 cm by 50 um piece of fused silica tubing obtained from Polymicro Technologies. That solute was dissolved in water. The absorbance of the sample solutions were referenced against the water. The results are shown in FIG. 4 and illustrate that with the static approach the sensitivity of the signal is better by a factor of 4.80 using the sapphire ball lens 305 than using straightforward transverse illumination. Curves 41–43 are static measurements of absorption by vacuum aspiration to illustrate the sensitivity of UV detection with a sapphire lens capillary cell versus a capillary transverse illumination. Curve 41 is for a sapphire lens and 0.5 mm aperture. It exhibits a slope of $2.49 \cdot 10^{-4}$ AU/$\mu$g/ml and an MDC of 0.78 $\mu$g/ml. Curve 42 is for a sapphire lens with a 0.8 mm aperture. Curve 43 is for a transverse illumination of the capillary. This curve exhibits a slope of $0.517 \cdot 10^{-4}$ AU/$\mu$g/ml and an MDC of 3.7 $\mu$g/ml. The curves in FIGS. 5A and 5B are electropherograms of horse heart myoglobin by pulse injection of 10 $\mu$g/ml. The curve in FIG. 5A is for transvere illumination of a capillary cell and exhibits a signal to noise ratio of 1.9 and an MDC of 10.5 $\mu$g/ml. The curve in FIG. 5B exhibits a signal to noise ratio of 4.2 and an MDC of 4.8 $\mu$g/ml. (Sensitivity is defined as the slope of the signal in absorbance units, i.e. AU, versus concentration, measured in $\mu$g/ml.). The minimum detectable concentration, MDC, is defined as the analyte concentration at which the signal is at least twice as large as the noise of the system without the analyte. In the first approach the MDC decreased by a factor of 4.74, from 3.7 $\mu$g/ml to 0.78 $\mu$g/ml.

In the second approach, signal to noise measurements were made using impulse input and capillary electrophoresis. Input was achieved by vacuum injection of a 10 $\mu$g/ml aqueous solution of horse heart myoglobin at 5 inches of Hg. (See related copending patent application Ser. No. 156,430, entitled CAPILLARY ELECTROPHORESIS, filed Feb. 16, 1988, by Lauer et al., and its continuation case 07/463,796 incorporated herein by reference, for a discussion of vacuum injection methods.) The run voltage was 20 KV with a capillary temperature of 30 degrees C. The run buffer was 20 mM citrate, pH 2. The results are shown in FIG. 5, and illustrate that using this impulse input and electrophoresis approach, the signal to noise ratio is enhanced by a factor of 2.2 using the sapphire ball lens detection system of the invention as opposed to simple transverse illumination. This also means that the MDC in the second approach improves by a factor of 2.2 at or near the detection limit of the system.

Those skilled in the art will realize there are many variations that can be made to the above apparatus without deviating from the principles of the invention. For example, the particular material used for the lens holder may be varied, different materials could be used for the lens itself provided the geometry were accomodated to achieve radial incidence on the capillary tube, and the particular dimensions may vary from one capillary system to another. Also, it should be clear that the results are not dependent on whether one is performing liquid chromatography or capillary electrophoresis, supercritical fluid chromatography, hydrodynamic chromatography, or measurements in other kinds of capillary systems. Further, although the specific embodiment presented deals with UV absorption, the concept of the invention is clearly extendable to other wavelengths. Similarly, should it be desired to use such a system for fluorescence detection, some alternative would likely be made in the direction of the exit aperture relative to the entrance aperture. Hence, it is intended that the invention not be limited to the particular embodiments described but that it should be construed in light of the following claims.

We claim:

1. An apparatus for enhancing signal to noise ratio in the detection of electromagnetic radiation traversing a capillary tube of outer diameter on the order of or less than 375 microns and center bore diameter on the order of 50 microns, comprising:
   a capillary of outer diameter on the order of or less than 375 microns and having center bore of diameter on the order of or less than 50 microns;
   a lens; and
   holding means for holding said lens and the capillary tube, said holding means having an aperture so that said aperture and said lens together define an optic axis, said holding means configured to hold the capillary tube such that the center of the capillary tube traverses the optic axis;
   said lens having a focal length and being held at such a position by said holding means such that electromagnetic radiation incident on said aperture is focussed to pass substantially radially through the center bore of the capillary tube.

2. An apparatus as in claim 1 wherein said holding means comprises two mating parts, a first part having said aperture and configured for holding said lens, and a second part which when placed into juxtaposition with said first part holds capillary tube so that the center of the capillary tube traverses the optic axis, said second part having an exit aperture for permitting detection of electromagnetic radiation that has traversed the capillary tube from the lens.

3. An apparatus for enhancing the signal to noise ratio in the detection of electromagnetic radiation traversing a capillary tube, comprising:
 a ball lens; and
 holding means for holding said lens and the capillary tube, said holding means having an aperture so that said aperture and said ball lens together define an optic axis, said holding means configured to hold the capillary tube such that the center of the capillary tube traverses the optic axis;
 said ball lens having a focal length and being held at such a position by said holding means such that electromagnetic radiation incident upon said aperture is focussed to pass substantially radially through the capillary tube.

4. An apparatus as in claim 3 wherein said holding means holds the capillary tube in contact with said ball lens.

5. An apparatus as in claim 4 wherein said ball lens is made of sapphire.

6. An apparatus as in claim 3 wherein said holding means includes a deformable substance within which is a hole of diameter a few percent smaller than the diameter of the ball lens and wherein the spherical lens is press fit into this hole.

7. An apparatus for enhancing signal to noise ratio in the detection of electromagnetic radiation traversing a capillary tube, comprising:
 a ball lens;
 holding means for holding said ball lens and the capillary tube, said holding means having an aperture that, in conjunction with said lens, defines an optic axis, said holding means having a trapezoidal groove within which is fitted the capillary tube to hold the capillary tube in contact with the ball lens such that the center of the capillary tube traverses the optic axis;
 said ball lens having a focal length such that electromagnetic radiation incident on said aperture is focussed to pass radially through the capillary tube.

8. An apparatus for enhancing signal to noise ratio in the detection of electromagnetic radiation traversing a capillary tube, comprising:
 a ball lens;
 holding means for holding said ball lens in contact with the capillary tube, said holding means having an aperture that, in conjunction with said lens, defines an optic axis that passes through the ball lens and the center of the capillary tube;
 said ball lens having a focal length such that electromagnetic radiation incident on said aperture is focussed to pass radially through the capillary tube.

9. A sample cell assembly for use in spectroscopy of samples in capillary chromatography comprising sample cell means having a cavity defined by a wall for containing a sample to be analyzed, and ball lens means in the form of a sphere mounted adjacent said wall for directing light from a source through said wall.

* * * * *